(12) United States Patent
Kasai et al.

(10) Patent No.: US 8,642,319 B2
(45) Date of Patent: Feb. 4, 2014

(54) OPTICAL-WAVEGUIDE SENSOR CHIP, METHOD OF MANUFACTURING THE SAME, METHOD OF MEASURING SUBSTANCE, SUBSTANCE-MEASURING KIT AND OPTICAL-WAVEGUIDE SENSOR

(75) Inventors: Shingo Kasai, Yokohama (JP); Ikuo Uematsu, Yokohama (JP); Ichiro Tono, Yokohama (JP); Tomohiro Takase, Sagamihara (JP); Isao Nawata, Yokohama (JP); Kayoko Oomiya, Yokohama (JP); Yuriko Oyama, Yokohama (JP); Tsutomu Honjoh, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 13/462,196

(22) Filed: May 2, 2012

(65) Prior Publication Data
US 2012/0213669 A1      Aug. 23, 2012

Related U.S. Application Data

(63) Continuation of application No. 12/266,023, filed on Nov. 6, 2008, now abandoned.

(30) Foreign Application Priority Data

Nov. 7, 2007  (JP) .................. 2007-290210
Oct. 24, 2008  (JP) .................. 2008-274708

(51) Int. Cl.
*C12M 1/34* (2006.01)
(52) U.S. Cl.
USPC .............. 435/287.2; 422/82.11; 435/288.7; 435/808; 436/164; 436/524; 436/525; 436/805

(58) Field of Classification Search
None
See application file for complete search history.

(56) References Cited

U.S. PATENT DOCUMENTS

| | | | |
|---|---|---|---|
| 4,979,821 A | 12/1990 | Schutt et al. | |
| 5,017,009 A | 5/1991 | Schutt et al. | |
| 5,631,170 A | 5/1997 | Attridge | |
| 2007/0081758 A1 | 4/2007 | Tono et al. | |

FOREIGN PATENT DOCUMENTS

| | | |
|---|---|---|
| CN | 1940529 A | 4/2007 |
| JP | 6-213892 A | 8/1994 |
| JP | 7-63760 A | 3/1995 |
| JP | 2001-21565 A | 1/2001 |
| JP | 2001-133460 A | 5/2001 |
| JP | 2005-156527 A | 6/2005 |
| JP | 2007-240361 A | 9/2007 |
| JP | 2008-216046 A | 9/2008 |
| JP | 2009-115665 A | 5/2009 |
| JP | 2010-71693 A | 4/2010 |
| WO | WO 2005/022155 A1 | 3/2005 |

OTHER PUBLICATIONS

Office Action issued on Jan. 8, 2013, in Japanese patent Application No. 2008-274708 with English translation.

*Primary Examiner* — Chris L Chin
(74) *Attorney, Agent, or Firm* — Oblon, Spivak, McClelland, Maier & Neustadt, L.L.P.

(57) ABSTRACT

An optical-waveguide sensor chip includes an optical waveguide having a first substance immobilized on the surface thereof, the first substance being specifically reactive with an analyte substance, and fine particles dispersed on the optical waveguide and having a second substance immobilized on the surface thereof, the second substance being specifically reactive with the analyte substance.

9 Claims, 11 Drawing Sheets

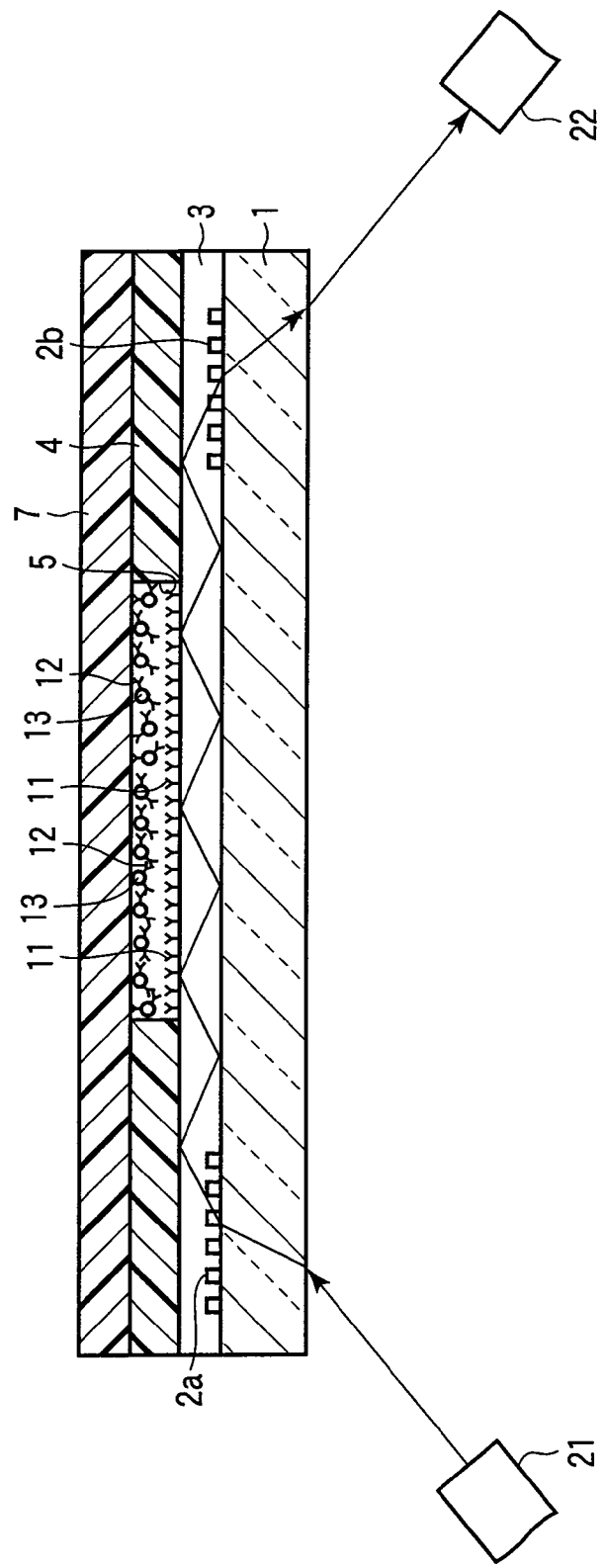
F I G. 3

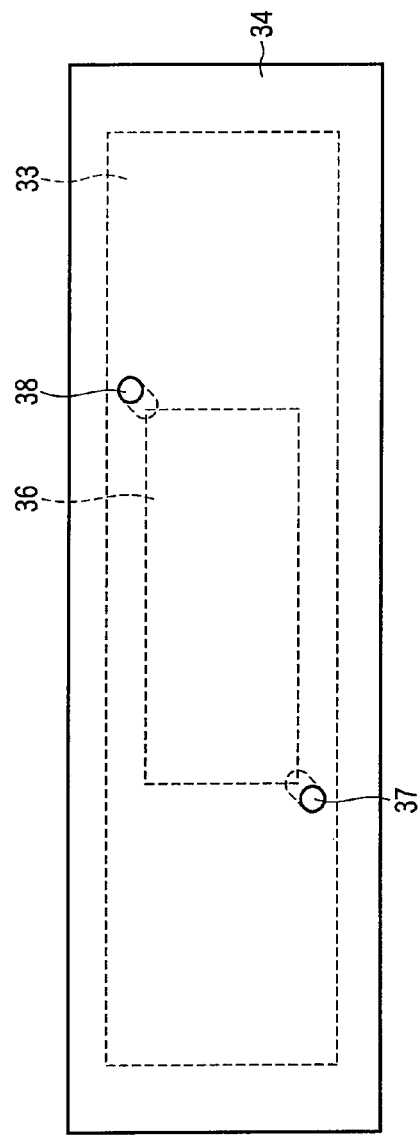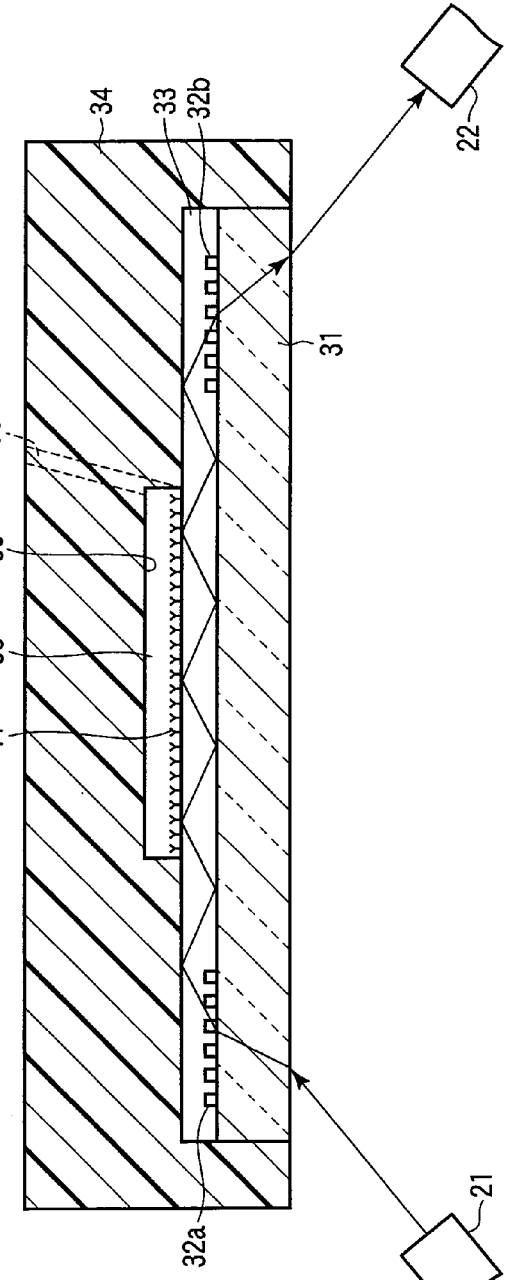
FIG. 8A
FIG. 8B

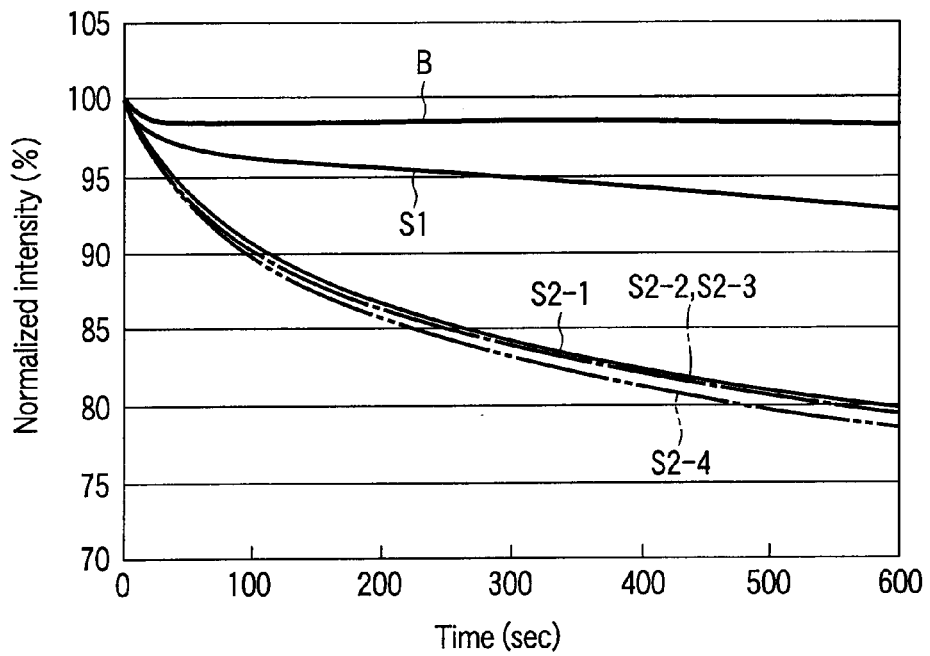
F I G. 12
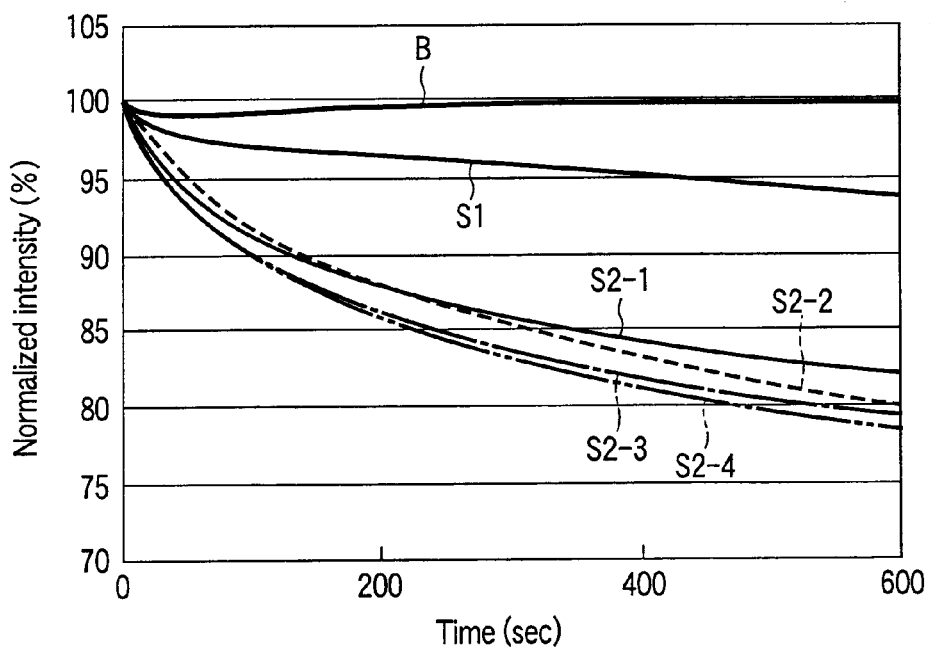
F I G. 13

OPTICAL-WAVEGUIDE SENSOR CHIP, METHOD OF MANUFACTURING THE SAME, METHOD OF MEASURING SUBSTANCE, SUBSTANCE-MEASURING KIT AND OPTICAL-WAVEGUIDE SENSOR

CROSS-REFERENCE TO RELATED APPLICATIONS

This application is a continuation of U.S. application Ser. No. 12/266,023 filed Nov. 6, 2008, and is based upon and claims the benefit of priority from prior Japanese Patent Applications No. 2007-290210, filed Nov. 7, 2007; and No. 2008-274708, filed Oct. 24, 2008, the entire contents of each of which are incorporated herein by reference.

BACKGROUND OF THE INVENTION

1. Field of the Invention

The present invention relates to an optical-waveguide sensor chip, a method of manufacturing the optical-waveguide sensor chip, a method of measuring a substance, a substance-measuring kit and an optical-waveguide sensor.

2. Description of the Related Art

Normally in conventional immunological assays by using antigen-antibody reaction, primary antibodies corresponding to the analyte such as protein in the analyte sample are immobilized on the surface of a well-shaped substrate. Particular amounts of an analyte sample solution, a secondary antibody solution, and a coloring reagent are added dropwise to the well sequentially. After dropwise addition of each solution, the well is washed with a particular washing water. These immunological assays are thus carried out in complicated procedure demanding addition and discharge of these reagents while weighed by the operator. These immunological assays demand an analyte sample in an amount of at least 5 µL to about 25 µL.

WO2005/022155 filed by the applicant discloses a concentration-determining method and a sensor chip demanding an analyte sample in an amount of 1 µL and allowing measurement of the concentration of the analyte substance in the analyte sample even when the volume of the analyte sample is inaccurate.

However, conventional immunological assays demand almost one hour for reaction between the primary antibody and the analyte sample and also for reaction between the analyte sample and the secondary antibody, leading to the complicated procedure described above. Accordingly, it takes as long as several hours to perform a series of procedure from collection of the analyte sample to completion of measurement. In addition, the amount of the analyte sample needed is large, and, for example in the case of blood test by using a small animal such as rat, one animal should be sacrificed for one examination of a few kinds of test items. As a result, it is often difficult to monitor change over time in the same sample.

BRIEF SUMMARY OF THE INVENTION

According to a first aspect of the present invention, there is provided an optical-waveguide sensor chip, comprising:

an optical waveguide having a first substance immobilized on the surface thereof, the first substance being specifically reactive with an analyte substance; and fine particles dispersed on the optical waveguide and having a second substance immobilized on the surface thereof, the second substance being specifically reactive with the analyte substance.

According to a second aspect of the present invention, there is provided an optical-waveguide sensor chip, comprising:

an optical waveguide having a first substance immobilized on the surface thereof, the first substance being specifically reactive with an analyte substance;

a supporting plate placed at a position facing the optical waveguide; and fine particles dispersed on the surface of the supporting plate facing the optical waveguide and having a second substance immobilized on the surface thereof, the second substance being specifically reactive with the analyte substance.

According to a third aspect of the present invention, there is provided a method of manufacturing an optical-waveguide sensor chip, comprising:

immobilizing a first substance on the surface of an optical waveguide, the first substance being specifically reactive with an analyte substance;

preparing a slurry contained fine particles having a second substance immobilized on the surface thereof, the second substance being specifically reactive with the analyte substance;

applying the slurry on the optical waveguide; and dispersing the fine particles on the optical waveguide by drying after the application.

According to a fourth aspect of the present invention, there is provided a method of manufacturing an optical-waveguide sensor chip, comprising:

immobilizing a first substance on the surface of an optical waveguide, the first substance being specifically reactive with an analyte substance;

preparing a slurry contained fine particles having a second substance immobilized on the surface thereof, the second substance being specifically reactive with the analyte substance;

applying the slurry on the surface of a supporting plate;

dispersing the fine particles on the supporting plate by drying after application; and placing the supporting plate at a position separated by a given distance from the optical waveguide such that a fine particle-dispersed face of the supporting plate is faced at the optical waveguide.

According to a fifth aspect of the present invention, there is provided a method of measuring a substance, comprising:

preparing an optical-waveguide sensor chip comprising an optical waveguide having a first substance immobilized on the surface thereof, the first substance being specifically reactive with an analyte substance, and fine particles dispersed on the optical waveguide and having a second substance immobilized on the surface thereof, the second substance being specifically reactive with the analyte substance;

dropping an analyte sample solution on the surface of the optical waveguide of the sensor chip to allow specific reaction between the first substance on the surface of the optical waveguide and the analyte substance in the analyte sample solution and also between the analyte substance and the second substance on the surface of the fine particles; and detecting the optical change caused by immobilizing the fine particles on the surface of the optical waveguide via the first substance and the analyte substance.

According to a sixth aspect of the present invention, there is provided a method of measuring a substance, comprising:

preparing an optical-waveguide sensor chip comprising an optical waveguide having a first substance immobilized on the surface thereof, the first substance being specifically reactive with an analyte substance;

preparing a dispersion of fine particles having a second substance immobilized on the surface thereof, the second substance being specifically reactive with the analyte substance;

dropping an analyte sample solution on the surface of the optical waveguide of the sensor chip to allow specific reaction between the first substance on the surface of the optical waveguide and the analyte substance in the analyte sample solution;

washing the optical waveguide surface;

dropping the dispersion of fine particles on the surface of the optical waveguide to allow specific reaction between the analyte substance in analyte sample solution and the second substance on the fine particles in the dispersion; and detecting the optical change caused by immobilizing the fine particles on the surface of the optical waveguide via the first substance and the analyte substance.

According to a seventh aspect of the present invention, there is provided a method of measuring a substance, comprising:

preparing an optical-waveguide sensor chip comprising an optical waveguide having a first substance immobilized on the surface thereof, the first substance being specifically reactive with an analyte substance;

previously mixing an analyte sample solution with fine particles having a second substance, which is specifically reactive with the analyte substance, immobilized on the surface thereof to allow specific reaction between the second substance on the fine particles and the analyte substance in analyte sample solution;

dropping a liquid mixture obtained on the surface of the optical waveguide of the sensor chip to allow specific reaction between the first substance on the surface of the optical waveguide and the analyte substance in analyte sample solution which is reacted with the second substance on the fine particles; and detecting the optical change caused by immobilizing the fine particles on the surface of the optical waveguide via the first substance and the analyte substance.

According to an eighth aspect of the present invention, there is provided a method of measuring a substance, comprising:

preparing an optical-waveguide sensor chip comprising an optical waveguide having a first substance immobilized on the surface thereof, the first substance being specifically reactive with an analyte substance;

preparing a dispersion of fine particles having a second substance immobilized on the surface thereof, the second substance being specifically reactive with the analyte substance;

dropping an analyte sample solution on the surface of the optical waveguide of the sensor chip to allow specific reaction between the first substance on the surface of the optical waveguide and the analyte substance in the analyte sample solution;

dropping the dispersion of fine particles on the surface of the optical waveguide to allow specific reaction between the analyte substance and a second substance on the fine particles in the dispersion; and detecting the optical change caused by immobilizing the fine particles on the surface of the optical waveguide via the first substance and the analyte substance.

According to a ninth aspect of the present invention, there is provided a method of measuring a substance, comprising:

preparing an optical-waveguide sensor chip comprising an optical waveguide having a first substance immobilized on the surface thereof, the first substance being specifically reactive with an analyte substance;

preparing a dispersion of fine particles having a second substance immobilized on the surface thereof, the second substance being specifically reactive with the analyte substance;

dropping the dispersion of fine particles on the surface of the optical waveguide of the sensor chip;

dropping the analyte sample solution on the surface of the optical waveguide which is previously carried out a dropping of the dispersion to allow specific reaction between the first substance on the surface of the optical waveguide and the analyte substance in the analyte sample solution and also between the analyte substance and the second substance on the surface of the fine particles in the dispersion; and detecting the optical change caused by immobilizing the fine particles on the surface of the optical waveguide via the first substance and the analyte substance.

According to a tenth aspect of the present invention, there is provided a method of measuring a substance, comprising:

preparing an optical-waveguide sensor chip comprising an optical waveguide having a first substance immobilized on the surface thereof, the first substance being specifically reactive with an analyte substance, a supporting plate placed at a position facing the optical waveguide, and fine particles dispersed on the surface of the supporting plate facing the optical waveguide and having a second substance immobilized on the surface thereof, the second substance being specifically reactive with the analyte substance;

injecting an analyte sample solution into the space between the optical waveguide and the supporting plate of the sensor chip to allow specific reaction between the first substance on the surface of the optical waveguide and an analyte substance in the analyte sample solution and also between the analyte substance and the second substance on the fine particles dispersed on the supporting plate; and detecting the optical change caused by immobilizing the fine particles on the surface of the optical waveguide via the first substance and the analyte substance.

According to an eleventh aspect of the present invention, there is provided a substance-measuring kit comprising, in combination:

an optical-waveguide sensor chip comprising an optical waveguide having a first substance immobilized on the surface thereof, the first substance being specifically reactive with an analyte substance, and a cap formed on the optical waveguide and having a dent for forming a measurement region with the optical waveguide and having inlet and outlet holes for communication with the measurement region; and a package accommodated a dispersion of fine particles having a second substance immobilized on the surface thereof, the second substance being specifically reactive with the analyte substance.

According to a twelfth aspect of the present invention, there is provided a method of measuring a substance by using the substance-measuring kit, comprising:

dropping an analyte sample solution on the surface of the optical waveguide in the measurement region through the inlet hole of the cap of optical-waveguide sensor chip to allow specific reaction between the first substance immobilized on the surface of the optical waveguide and the analyte substance in analyte sample solution;

introducing the dispersion of fine particles in the package on the surface of the optical waveguide in the measurement region through the cap inlet hole and discharging the dispersion through the outlet hole to allow specific reaction between the analyte substance specifically reacted with the first substance and the second substance on the surface of the fine particles; and detecting the optical change caused by immobilizing the fine particles on the surface of the optical waveguide via the first substance and the analyte substance.

According to a thirteenth aspect of the present invention, there is provided an optical-waveguide sensor, comprising:

an optical-waveguide sensor chip comprising an optical waveguide having a first substance immobilized on the surface thereof, the first substance being specifically reactive with an analyte substance, and fine particles dispersed on the optical waveguide and having a second substance immobilized on the surface thereof, the second substance being specifically reactive with the analyte substance;

a light source emitting a light into the optical waveguide; and a light-receiving device receiving the light emitted from the optical waveguide.

According to a fourteenth aspect of the present invention, there is provided an optical-waveguide sensor, comprising:

an optical-waveguide sensor chip comprising an optical waveguide having a first substance immobilized on the surface thereof, the first substance being specifically reactive with an analyte substance, a supporting plate placed at a position facing the optical waveguide, and fine particles dispersed on the surface of the supporting plate facing the optical waveguide and having a second substance immobilized on the surface thereof, the second substance being specifically reactive with the analyte substance;

a light source emitting a light into the optical waveguide; and a light-receiving device receiving the light emitted from the optical waveguide.

BRIEF DESCRIPTION OF THE SEVERAL VIEWS OF THE DRAWING

FIG. 3 is a cross-sectional view illustrating an optical-waveguide sensor having an optical-waveguide sensor chip in a second embodiment;

FIG. 8A and FIG. 8B are cross-sectional views illustrating an optical-waveguide sensor chip of a substance-measuring kit in a fifth embodiment;

FIG. 12 is a graph showing a change in laser beam intensity over time in an insulin concentration measurement of Example 3; and FIG. 13 is a graph showing a change in laser beam intensity over time in an insulin concentration measurement of Example 4.

DETAILED DESCRIPTION OF THE INVENTION

Figure 1:
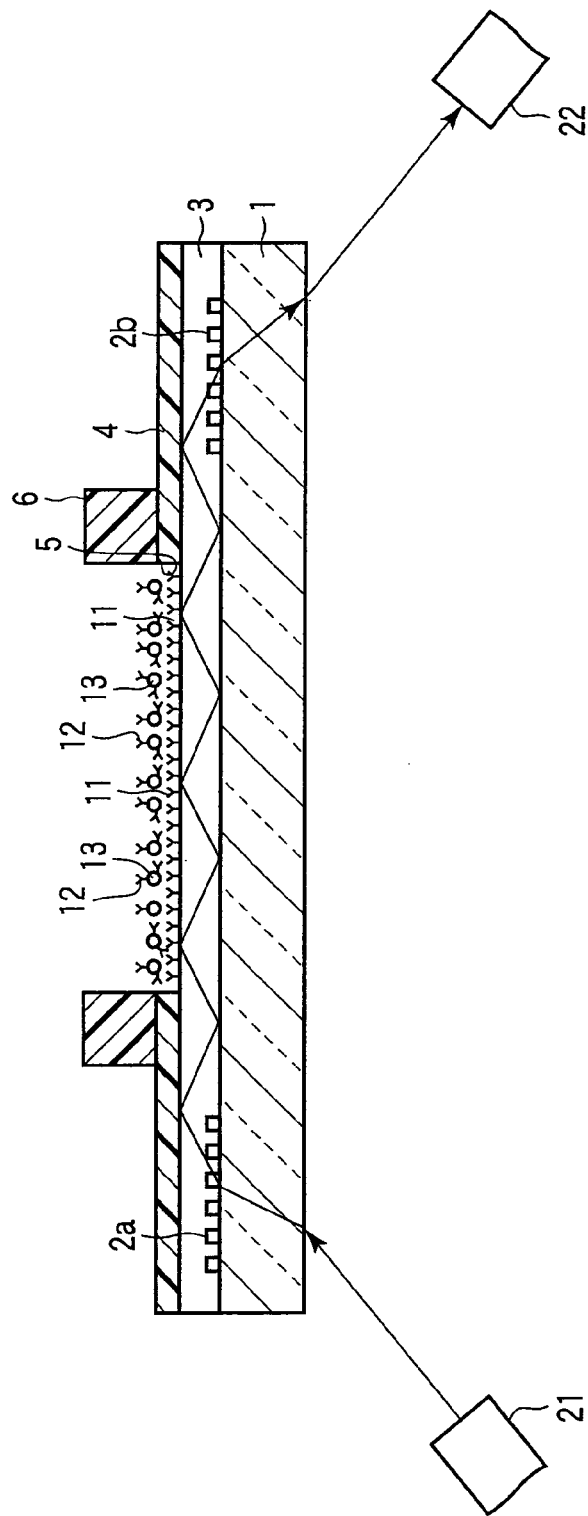
FIG. 1 is a cross-sectional view illustrating an optical-waveguide sensor having an optical-waveguide sensor chip in a first embodiment.

Hereinafter, an optical-waveguide sensors, methods of producing an optical-waveguide sensor chip, methods of determining a substance, and kits and optical-waveguide sensors for measurement of a substance according to the embodiments of the present invention will be described in detail.

First Embodiment

An optical-waveguide sensor chip in the first embodiment comprises an optical waveguide having a first substance immobilized on the surface thereof. The first substance is specifically reactive with an analyte substance. Fine particles are dispersed on the optical waveguide and having a second substance immobilized on the surface thereof. The second substance is specifically reactive with the analyte substance.

The analyte substances include, for example, blood, blood sera, blood plasmas, biological samples, and proteins, peptides and genes contained for example in foods. Typical examples thereof include, but are not limited to, hapten hormones such as insulin, casein, β-lactoglobulin, ovalbumin, calcitonin, C-peptide, leptin, β-2-microglobulin, retinol-binding protein, α-1-microglobulin, α-fetoprotein, oncofetal antigens, troponin-I, glucagon-like peptides, insulin-like peptides, tumor growth factors, fibroblast growth factors, platelet growth factors, epidermal growth factors, cortisol, triiodothyronine, and thyroxin; pharmaceuticals such as digoxin and theophylline; infectious substances such as microbes and viruses; hepatitis antibody, IgEs, soluble proteins including major buckwheat protein complexes and peanut Arah2; and the like. A similar analyte substance is used in the following second to fifth embodiments.

For example, a planar optical waveguide may be used as the optical waveguide. The planar optical waveguide can be formed, for example, by using a thermosetting resin such as phenol resin or epoxy resin or a nonalkali glass. Specifically, the material for use is preferably a material transmitting a particular light, in particular of an epoxy resin containing polystyrene as its primary structure. The first substance specifically reacted with an analyte substance in the analyte sample is immobilized on the planar optical waveguide by hydrophobic interaction of the substance with the surface previously hydrophobilized, for example, with a silane-coupling agent. For example if the analyte substance in the analyte sample is an antigen, an antibody can be used as the first substance.

The phrase "fine particles dispersed on the optical waveguide" means that the fine particles are dispersed directly or indirectly on the surface of the optical waveguide. The state of the "fine particles indirectly dispersed on the surface of the optical waveguide" is, for example, a state of fine particles dispersed on the optical waveguide surface via a blocking layer. The blocking layer contains, for example, a water-soluble substance such as polyvinylalcohol, bovine serum albumin (BSA), polyethylene glycol, phospholipid polymer, gelatin, or a sugar (e.g., sucrose or trehalose). The blocking layer may contain a protein inhibitor additionally.

The fine particles may be used, for example, resin beads such as latex beads (the trade name) made of polystyrene or a metal colloid such as gold colloid, inorganic oxide particles such as titanium oxide particles, or the like. The fine particles may be also used, for example a protein such as an albumin, a polysaccharide such as an agarose, or a non-metal particle such as silica particle, a carbon particle. In particular, latex beads and metal colloids are favorable. Among the latex beads above, blue latex beads are preferable if the light propagating through the optical waveguide described below is a red laser.

The fine particles preferably have a diameter of 50 nm to 10 µm.

For example, if the analyte substance in the analyte sample is an antigen, an antibody may be used as the second substance.

Hereinafter, the method of manufacturing the optical-waveguide sensor chip according to the first embodiment will be described.

First, a first substance is immobilized on the surface of an optical waveguide. The first substance is specifically reactive with an analyte substance. A second substance is then immobilized on the surface of fine particles, for example, by physical adsorption or by chemical binding for example via a carboxyl or amino group. The second substance is specifically reactive with the analyte substance. The fine particles having the second substance immobilized on the surface thereof are then dispersed in a physiological saline containing a water-soluble substance to prepare a slurry. The slurry is coated and dried on the optical waveguide, dispersing the fine particles on the optical waveguide, thereby manufacturing an optical-waveguide sensor chip.

The water-soluble substance for use in such a production method may be, for example, polyvinylalcohol, bovine serum albumin (BSA), polyethylene glycol, a phospholipid polymer, gelatin, or a sugar (such as sucrose or trehalose). The drying is preferably freeze drying, for improvement of dispersion of the fine particles.

The optical-waveguide sensor chip according to the first embodiment will be described below specifically with reference to FIG. 1. FIG. 1 is a cross-sectional view illustrating the optical-waveguide sensor chip according to the first embodiment.

Two gratings, an incident-sided grating 2a and an outgoing-sided grating 2b, are formed on both terminals of the major face of the glass substrate 1, respectively. These gratings 2a and 2b are made, for example, of titanium oxide (TiO$_2$), tin oxide (SnO$_2$), zinc oxide, lithium niobate, gallium arsenide (GaAs), indium tin oxide (ITO), polyimide, or the like. For example, a planar optical waveguide 3 of a thermosetting resin is formed on the major face of the substrate 1 having the gratings 2a and 2b. A low-refractive index resin film 4 is coated on the planar optical waveguide 3. The low-refractive index resin for use is, for example, a commercially available poly(perfluorobutenylvinylether), Cytop (registered trade name) manufactured by Asahi Glass Co., Ltd. or the like. The low-refractive index resin film 4 has, for example, a rectangular reaction hole 5 formed, so that part of the planar optical waveguide 3 located in the region between gratings 2a and 2b is exposed in the opening. A frame-shaped cell wall 6 is formed on the low-refractive index resin film 4, as it surrounds the reaction hole 5 exposing the planar optical waveguide 3.

A first substance 11 is immobilized on the surface of the planar optical waveguide 3 exposed in the reaction hole (measurement region) 5 by hydrophobilization treatment, for example, with a silane-coupling agent. The first substance is specifically reactive with an analyte substance. The fine particles 13 having a second substance 12 immobilized on the surface thereof are dispersed, for example, by coating and freeze-drying a slurry containing the fine particles and a water-soluble substance on the planar optical waveguide 3. The second substance is specifically reactive with the analyte substance.

The optical-waveguide sensor according to the first embodiment has a light source (e.g., red laser diode) 21 emitting light through the incident-sided grating 2a of the optical-waveguide sensor chip described above into the planar optical waveguide 3 and a light-receiving device (e.g., photodiode) 22 receiving the light from the outgoing-sided grating 2b.

Hereinafter, the method of measuring the substance by using the optical-waveguide sensor described above will be described below with reference to FIGS. 2A to 2C.

Figure 2A:
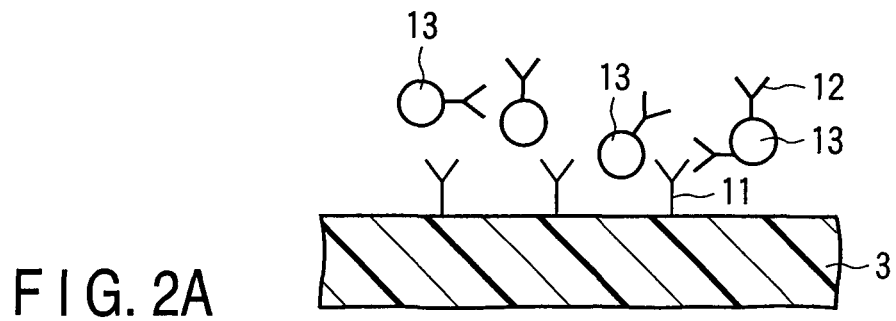
FIG. 2A, FIG. 2B and FIG. 2C are schematic views illustrating the step of measuring an analyte substance in analyte sample in the first embodiment.
Figure 2B:
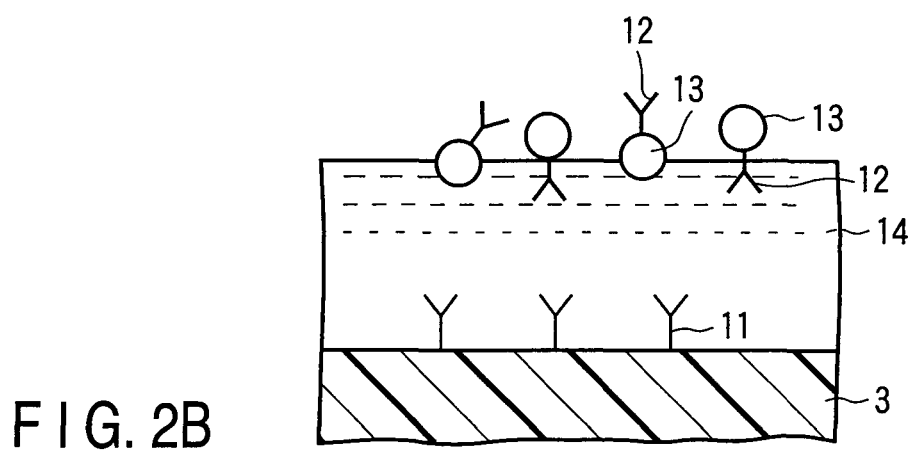

First, an optical-waveguide sensor chip shown in FIG. 2A is prepared. The sensor chip comprises a substrate 1 having gratings 2a and 2b. A planar optical waveguide 3 is formed on the major face of the substrate 1 containing gratings 2a and 2b. A low-refractive index resin film 4 is coated on the planar optical waveguide 3, forming for example a rectangular reaction hole 5 as an opening, so that part of the planar optical waveguide 3 located in the region between gratings 2a and 2b is exposed. A first substance (e.g., first antibody) 11 is immobilized on the surface of the planar optical waveguide 3 exposed in the reaction hole 5. The first antibody 11 is specifically reactive with an analyte substance (e.g., antigen) in an analyte sample. A plurality of fine particles 13 having a second substance (e.g., second antibody) 12 immobilized on the surface thereof are dispersed on the planer optical waveguide 3. The second antibody 12 is specifically reactive with the second antibody.

Then, an analyte sample solution is dropped on the surface of the planar optical waveguide 3 including the region in the reaction hole 5. At this time, if there is no antigen, which is specifically reactive with the first antibody 11 on the surface of the planar optical waveguide 3 and the second antibody 12 on the surface of the fine particles 13, respectively, in the analyte sample solution dropped, the second antibody 12 on the fine particles 13 does not bind to the first antibody 11 on the planar optical waveguide 3. Therefore, the fine particles 13 are dispersed in the analyte sample solution 14, as shown in FIG. 2B. Even if a red laser beam is irradiated from the red laser diode 21 through the incident-sided grating 2a to the planar optical waveguide 3 in the state and an evanescent light is generated in the region close to the surface (surface exposed in reaction hole 5) by propagation through the planar optical waveguide 3, since the fine particles 13 are dispersed in the analyte sample solution 14, the fine particles 13 are predominantly present in the evanescent light region. For this reason, the fine particles 13 are predominantly involved in absorption or scattering of the evanescent light, causing almost no decay in intensity of the evanescent light. As a result, the red laser beam from the outgoing-sided grating 2b retains its laser beam intensity almost entirely when it is received by the photodiode 22.

Figure 2C:
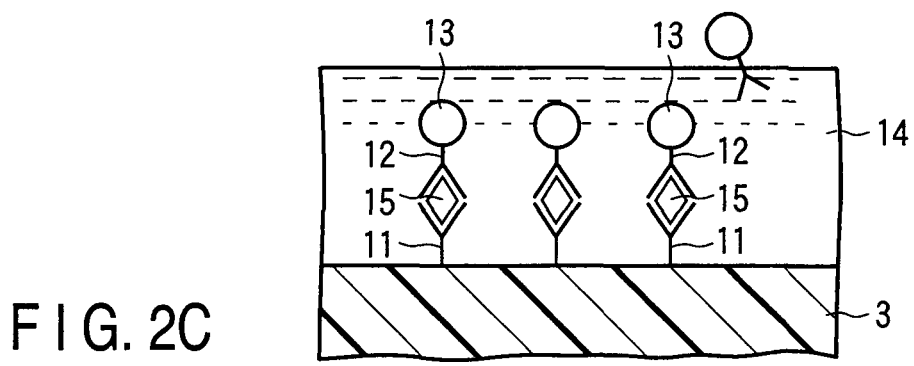

On the other hand, if there is an antigen in the analyte sample solution 14 applied dropwise, the antigen 15 binds to the first antibody 11 on the surface of the planar optical waveguide 3 by antigen-antibody reaction, and the second antibody 12 on the surface of the fine particles 13 binding to the antigen 15 by antigen-antibody reaction, as shown in FIG. 2C. Thus, the first antibody 11 on the surface of the planar optical waveguide 3 and the second antibody 12 on the surface of the fine particles 13 bind to each other via the antigen 15 by antigen-antibody reaction, resulting in immobilization of the fine particles 13 on the surface of the planar optical waveguide 3.

If a red laser beam is irradiated from a red laser diode 21 through the incident-sided grating 2a onto the planar optical waveguide 3 and propagated through the planar optical waveguide 3 for generation of evanescent light in the region close to the surface (surface exposed in reaction hole 5) immediately after dropping of the analyte sample solution, the fine particles 13, which are immobilized on the planar optical waveguide 3, are present in the evanescent light region. Thus, the fine particles 13 are involved in absorption or scattering of the evanescent light, leading to decay in intensity of the evanescent light. As a result, the intensity of the red laser beam released the outgoing-sided grating 2b and received by the photodiode 22 declines gradually over time under the influence of the immobilized fine particles 13.

The deterioration rate in intensity of the laser beam received by the photodiode 22 is proportional to the amount of the fine particles 13 immobilized on the planar optical waveguide 3, i.e., the concentration of the antigen participating in the antigen-antibody reaction in the analyte sample solution 14. Thus, a calibration curve showing the relationship between the antigen concentration and the deterioration rate in laser beam intensity is formed previously, by forming a curve showing deterioration in laser beam intensity over time by using an analyte sample solution having a known antigen concentration and determining the deterioration rate in laser beam intensity at a particular time on the curve. It is possible to determine the concentration of the antigen in the analyte sample solution by determining the deterioration rate in laser beam intensity at a particular time from the curve of deterioration in laser beam intensity over time as determined by the method above and comparing the deterioration rate in laser beam intensity with the calibration curve.

It is possible to increase dispersion of the fine particles, by dispersing the fine particles together with a water-soluble substance on the planar optical waveguide during the concentration measurement. The combined use thereof leads to solubilization of the fine particles and the copresent water-soluble substance, facilitating movement of the fine particles during dropwise application of the analyte sample solution on the planar optical waveguide and also permitting smooth reaction between the analyte substance and the second substance on fine particles in the analyte sample solution.

As described above, the first embodiment provides an optical-waveguide sensor chip demanding a small amount of an analyte sample (e.g., 10 μL or less) and allowing quantitative determination of the concentration of the analyte substance in analyte sample only by a single operation of applying the analyte sample in the measurement region dropwise, a production method thereof, and an optical-waveguide sensor containing the same.

Also in the first embodiment, the present invention provides a method of measuring a substance that demands a small amount of analyte sample (e.g., 10 μL or less) and allows quantitative determination of the concentration of the analyte substance in analyte sample only by a single operation of applying the analyte sample dropwise in the measurement region.

Second Embodiment

An optical-waveguide sensor chip in the second embodiment comprises an optical waveguide having a first substance immobilized on the surface thereof. The first substance is specifically reactive with an analyte substance. A supporting plate is placed at a position facing the optical waveguide. Fine particles are dispersed on the surface of the supporting plate facing the optical waveguide. The fine particles have a second substance immobilized on the surface thereof. The second substance is specifically reactive with the analyte substance.

For example, a planar optical waveguide can be used as the optical waveguide. Similarly to the first embodiment described above, the planar optical waveguide may be formed with a thermosetting resin or a nonalkali glass.

A first substance which is specifically reactive with an analyte substance in the analyte sample is immobilized on the planar optical waveguide in a manner similar to the method described in the first embodiment. For example, if the analyte substance in the analyte sample is an antigen, the first substance for use may be an antibody.

As described in the first embodiment, the fine particles may be used resin beads such as latex beads (the trade name) made of polystyrene, a metal colloid such as gold colloid, inorganic oxide particles such as titanium oxide particles, or the like. The fine particles may be also used, for example a protein such as an albumin, a polysaccharide such as an agarose, or a non-metal particle such as silica particle, a carbon particle. In particular, latex beads and noble metal colloids are preferable. The fine particles preferably have a diameter of 50 nm to 10 μm.

For example, if the analyte substance in analyte sample is an antigen, the second substance for use may be an antibody.

Hereinafter, the method of manufacturing the optical-waveguide sensor chip according to the second embodiment will be described.

First, a first substance is immobilized on the surface of an optical waveguide. The first substance is specifically reactive with an analyte substance. A second substance is then immobilized on the surface of fine particles, for example, by physical adsorption or chemical binding via a carboxyl or amino group and the like. The second substance is specifically reactive with the analyte substance in analyte sample. The fine particles are dispersed in physiological saline containing a water-soluble substance to prepare a slurry. The slurry is applied and dried on the surface of the supporting plate to disperse the fine particles on the supporting plate. Then, the supporting plate is placed at a position separated by a given distance from the optical waveguide such that a fine particle-dispersed face of the supporting plate is faced at the optical waveguide, thereby manufacturing an optical-waveguide sensor chip.

The water-soluble substance used in such a production method may be, for example, polyvinylalcohol, bovine serum albumin (BSA), polyethylene glycol, a phospholipid polymer, gelatin, or a sugar (such as sucrose or trehalose). The drying is preferably freeze-drying, for improvement in dispersion of the fine particles.

The optical-waveguide sensor according to the second embodiment will be described below, specifically with reference to FIG. 3. FIG. 3 is a cross-sectional view illustrating the optical-waveguide sensor chip according to the second embodiment.

Two gratings, an incident-sided grating 2a and an outgoing-sided grating 2b for example of titanium oxide, are formed on both terminals of the major face of the glass substrate 1, respectively. A planar optical waveguide 3, for example, of a thermosetting resin is formed on the major face of the substrate 1 including the gratings 2a and 2b. A low-refractive index resin film 4 is coated on the planar optical waveguide 3. The low-refractive index resin film 4 has, for example, a rectangular reaction hole 5 formed therein, so that part of the planar optical waveguide 3 located in the region between gratings 2a and 2b is exposed in the opening. A supporting plate 7 for example of a synthetic resin is formed on the low-refractive index resin film 4, as it covers the reaction hole 5. A hole for dropwise application of the analyte sample solution (not shown in the figure) is formed in the region of the reaction hole 5 on the surface of the supporting plate 7. A first substance 11 is immobilized on the surface of the planar optical waveguide 3 exposed in the reaction hole (measurement region) 5 by hydrophobilization treatment for example by using a silane-coupling agent. The first substance is specifically reactive with the analyte substance in analyte sample The fine particles 13 having a second substance immobilized on the surface thereof are dispersed on the surface (underside) of supporting plate 7 exposed in the reaction hole 5 and facing the planar optical waveguide 3. The fine particles 13 are dispersed, for example, by coating a slurry containing the fine particles and a water-soluble substance on the surface of the supporting plate and freeze drying the resulting plate. The second substance is specifically reactive with the analyte substance.

The optical-waveguide sensor according to the second embodiment has a light source (e.g., red laser diode) 21 emitting light through the incident-sided grating 2a of the optical-waveguide sensor chip described above into the planar optical waveguide 3 and a light-receiving device (e.g., photodiode) 22 receiving the light from the outgoing-sided grating 2b.

Hereinafter, the method of measuring a substance by using the optical-waveguide sensor described above will be described with reference to FIGS. 4A to 4C.

Figure 4A:
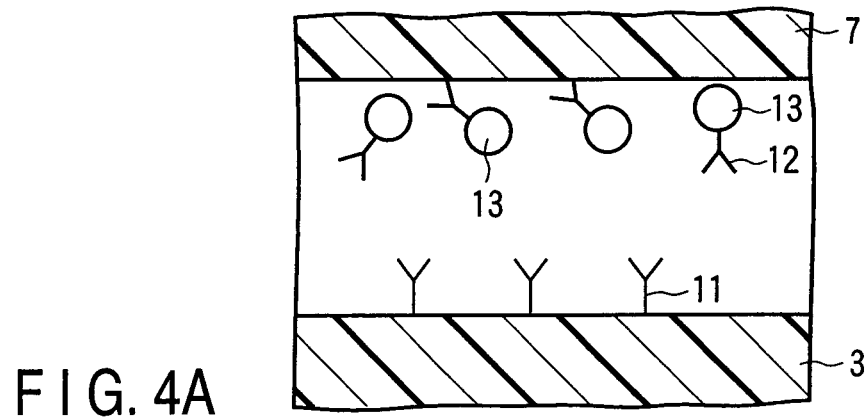
FIG. 4A, FIG. 4B and FIG. 4C are schematic views illustrating the step of measuring a substance in the second embodiment.

First, an optical-waveguide sensor chip shown in FIG. 4A is prepared. The sensor chip comprises a substrate 1 having gratings 2a and 2b. A planar optical waveguide 3 is formed on the major face of the substrate 1 containing gratings 2a and 2b. A low-refractive index resin film 4 is coated on the planar optical waveguide 3, forming for example a rectangular reaction hole 5 as an opening, so that part of the planar optical waveguide 3 located in the region between gratings 2a and 2b is exposed. A first substance (e.g., first antibody) 11 is immobilized on the surface of the planar optical waveguide 3 exposed in the reaction hole 5. The first antibody 11 is specifically reactive with an analyte substance (e.g., antigen) in an analyte sample. A supporting plate 7 is formed on the low-refractive index resin film 4, as it covers the reaction hole 5. A plurality of fine particles 13 having a second substance (e.g., second antibody) 12 immobilized on the surface thereof are dispersed on the underside of the supporting plate 7 exposed in the reaction hole 5. The second antibody 12 is specifically reactive with the second antibody.

Figure 4B:
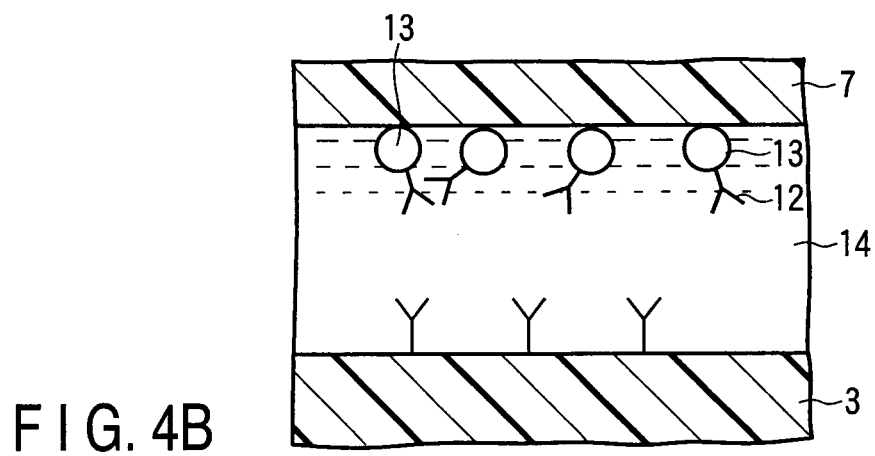

An analyte sample solution is then dropped into the reaction hole 5 through an analyte sample solution-dropping hole (not shown in the figure). As shown in FIG. 4B, if there is no antigen, which is specifically reactive with the first antibody 11 on the surface of the planar optical waveguide 3 and the second antibody 12 on the surface of the fine particles 13, respectively, in the analyte sample solution dropped, the second antibody 12 on the fine particles 13 does not bind to the first antibody 11 on the planar optical waveguide 3. Therefore, the fine particles 13 are dispersed in the analyte sample solution 14. Even if a red laser beam is irradiated from the red laser diode 21 through the incident-sided grating 2a to the planar optical waveguide 3 in the state, and an evanescent light is generated in the region close to the surface (surface exposed in reaction hole 5) by propagation through the planar optical waveguide 3, since the fine particles 13 are dispersed in the analyte sample solution 14, the fine particles 13 are predominantly present in the evanescent light region. Thus, the fine particles 13 are predominantly involved in absorption or scattering of the evanescent light, causing almost no decay in intensity of the evanescent light. As a result, the red laser beam from the outgoing-sided grating 2b retains its laser beam intensity almost entirely when it is received by the photodiode 22.

Figure 4C:
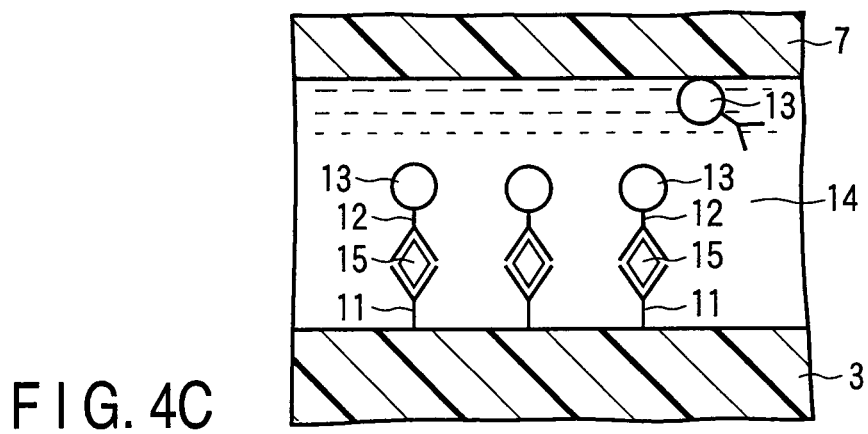

Alternatively if there is an antigen in the analyte sample solution 14 applied dropwise, the antigen 15 binds to the first antibody 11 on the surface of the planar optical waveguide 3 by antigen-antibody reaction, and the second antibody 12 on fine particles 13 binding to the antigen 15 in antigen-antibody reaction, as shown in FIG. 4C. Thus, the first antibody 11 on the planar optical waveguide 3 and the second antibody 12 on fine particles 13 bind to each other via the antigen 15 in antigen-antibody reaction, resulting in immobilization of the fine particles 13 on the planar optical waveguide 3.

If a red laser beam is irradiated from a red laser diode 21 through the incident-sided grating 2a onto the planar optical waveguide 3 and propagated through the planar optical waveguide 3 for generation of evanescent light in the region close to the surface (surface exposed in reaction hole 5) immediately after dropping of the analyte sample solution, the fine particles 13, which are immobilized on the planar optical waveguide 3, are present in the evanescent light region. Thus, the fine particles 13 are involved in absorption or scattering of the evanescent light, leading to decay in intensity of the evanescent light. As a result, the intensity of the red laser beam released the outgoing-sided grating 2b and received by the photodiode 22 declines gradually over time under the influence of the immobilized fine particles 13.

The deterioration rate in intensity of the laser beam received by the photodiode 22 is proportional to the amount of the fine particles 13 immobilized on the surface of the planar optical waveguide 3, i.e., the concentration of the antigen participating in the antigen-antibody reaction in the analyte sample solution 14. Therefore, a calibration curve showing the relationship between the antigen concentration and the deterioration rate in laser beam intensity is formed previously, by forming a curve showing deterioration in laser beam intensity over time by using an analyte sample solution having a known antigen concentration and determining the deterioration rate in laser beam intensity at a particular time on the curve. It is possible to determine the concentration of the antigen in the analyte sample solution by determining the deterioration rate in laser beam intensity at a particular time from the curve of deterioration in laser beam intensity over time as determined by the method above and comparing the deterioration rate in laser beam intensity with the calibration curve.

It is possible to increase dispersion of the fine particles by dispersing the fine particles together with a water-soluble substance on the planar optical waveguide during the concentration measurement. The combined use thereof leads to solubilization of the fine particles and the copresent water-soluble substance, facilitating movement of the fine particles during dropwise application of the analyte sample solution on the planar optical waveguide and also permitting smooth reaction between the analyte substance and the second substance on fine particles in the analyte sample solution.

Thus in the second embodiment, the invention provides an optical-waveguide sensor chip, demanding a small amount of an analyte sample (e.g., 10 μL or less) and allowing quantitative determination of the concentration of the analyte substance in analyte sample only by a single operation of applying the analyte sample in the measurement region dropwise, a production method thereof, and an optical-waveguide sensor containing the same.

Also in second embodiment, the invention provides a method of measuring a substance, demanding a small amount of analyte sample (e.g., 10 μL or less) and allowing quantitative determination of the concentration of the analyte substance in analyte sample only by a single operation of applying the analyte sample in the measurement region dropwise.

Third Embodiment

A method of measuring a substance according to the third embodiment will be described below.

First, an optical-waveguide sensor chip comprising an optical-waveguide sensor chip comprising an optical waveguide having a first substance immobilized on the surface thereof is prepared. The first substance is specifically reactive with an analyte substance. In addition, a dispersion of fine particles having a second substance immobilized on the surface thereof is prepared. The second substance is specifically reactive with the analyte substance.

Subsequently, an analyte sample solution is then dropped on the surface of the optical waveguide to allow a specific reaction between the first substance on the optical waveguide and the analyte substance in the analyte sample solution. Then, the surface of the optical waveguide is washed. Subsequently, the dispersion of fine particles is dropped on the surface of the optical waveguide to allow specific reaction between the analyte substance in analyte sample solution and the second substance on the fine particles. Then, the concentration of the analyte substance in the analyte sample solution is determined by detecting the optical change caused by the fine particles immobilized on the optical waveguide via the first substance and the analyte substance.

For example, a planar optical waveguide can be used as the optical waveguide. As described in the first embodiment, the planar optical waveguide may be formed with a thermosetting resin or a nonalkali glass. A first substance reacting specifically with an analyte substance in the analyte sample is immobilized on the planar optical waveguide in a manner similar to the method described in the first embodiment. For example, if the analyte substance in the analyte sample is an antigen, the first substance for use may be an antibody.

The washing is performed by using a washing solution such as a solution in combination of a buffer solution, a surfactant and others, phosphate buffered physiological saline (PBS) containing a surfactant, Tris-hydrochloric acid-buffered physiological saline, Good's buffer-buffered physiological saline, phosphate buffer solution, or the like.

Similarly to the first embodiment described above, the fine particles may be used resin beads such as latex beads (the trade name) made of polystyrene, a metal colloid such as gold colloid, inorganic oxide particles such as titanium oxide particles, or the like. The fine particles may be also used, for example a protein such as an albumin, a polysaccharide such as an agarose, or a non-metal particle such as silica particle, a carbon particle. In particular, latex beads and noble metal colloids are preferable. The fine particles preferably have a diameter of 50 nm to 10 μm.

For example, if the analyte substance in the analyte sample is an antigen, the second substance, which is immobilized on the fine particles in a manner similar to first embodiment, may be an antibody.

The fine particle dispersions include, for example, buffer solutions containing phosphoric acid, trishydroxymethylaminomethane, boric acid, acetic acid, citric acid, carbonic acid or the like or a Good's buffer; those containing a stabilizer such as bovine serum albumin (BSA), casein, or polyethylene glycol and a nonionic surfactant such as Tween or Triton-X; phosphate-buffered physiological saline (PBS), and the like.

The method of measuring a substance according to the third embodiment will be described specifically, with reference to the optical-waveguide sensor chip shown in FIG. 5 and FIGS. 6A to 6C.

Figure 5:
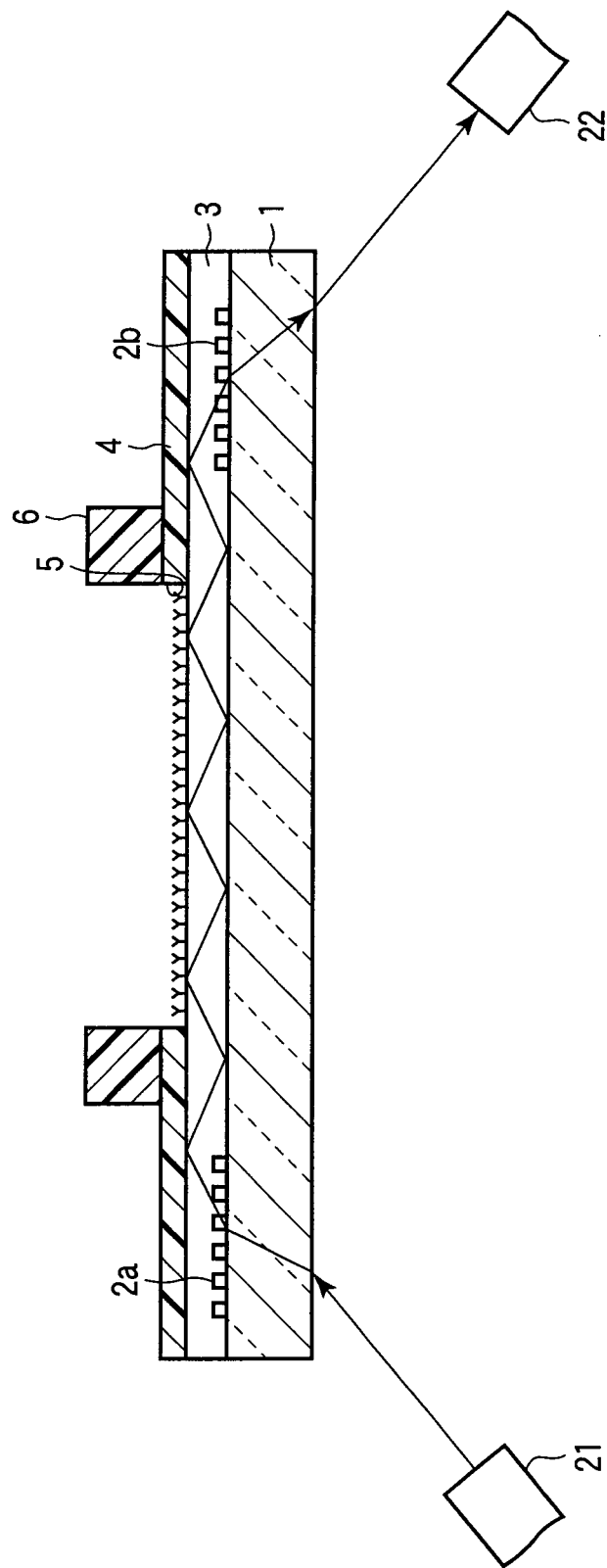
FIG. 5 is a cross-sectional view illustrating an optical-waveguide sensor chip for use in the method of measuring a substance according to a third embodiment.
Figure 6A:
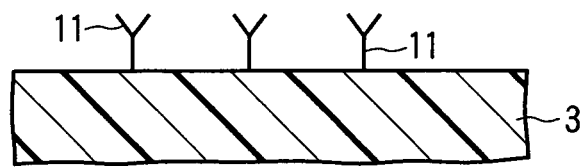
FIG. 6A, FIG. 6B and FIG. 6C are schematic views illustrating the step of measuring a substance in the third embodiment.

First, an optical-waveguide sensor chip shown in FIGS. 5 and 6A is prepared. The sensor chip comprises a structure similar to that shown in the first embodiment, except that there is no dispersion layer of the fine particles shown in FIG. 1. Thus, it has a substrate 1 having gratings 2a and 2b. The planar optical waveguide 3 is formed on the major face of the substrate 1 containing gratings 2a and 2b. A low-refractive index resin film 4 is coated on the planar optical waveguide 3 and, for example, a rectangular reaction hole 5 is formed therein as an opening in such a way that part of the planar optical waveguide 3 located in the region between gratings 2a and 2b is exposed. A first substance (e.g., first antibody) 11 is immobilized on the surface of the planar optical waveguide 3 exposed in the reaction hole 5. The first antibody 11 is specifically reactive with the analyte substance in analyte sample (e.g., antigen). As shown in FIG. 5, a laser oscillator (e.g., red laser diode) 21 emitting light to the incident-sided grating 2a is installed for measurement of the change in evanescent light from the planar optical waveguide 3 in the region corresponding to the reaction hole 5, and a photoelectric conversion device (photodiode) 22 is installed for receiving the light from the outgoing-sided grating 2b. In addition, a dispersion of fine particles having a second substance (second antibody) immobilized on the surface thereof is prepared. The second antibody is specifically reactive with the antigen.

Figure 6B:
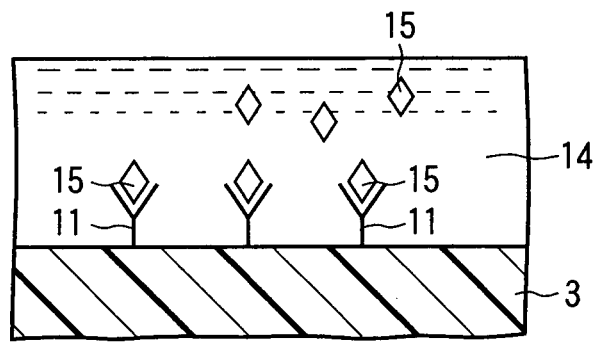

An analyte sample solution is then dropped he planar optical waveguide 3. At this time, as shown in FIG. 6B, the antigen 15 in the analyte sample solution binds to the first antibody 11 on the planar optical waveguide 3 by antigen-antibody reaction.

Figure 6C:
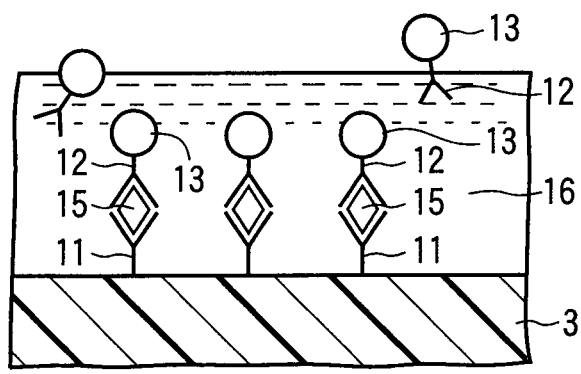

The antigen 15 remaining unreacted with the first antibody 11 on the surface of the planar optical waveguide 3 is then removed by washing treatment. The dispersion of fine particles 13 having second antibody 12 immobilized on the surface thereof is dropped on the surface of the planar optical waveguide 3. As shown in FIG. 6C, the antigen 15 in the analyte sample solution, which is bonded to the first antibody 11 on the planar optical waveguide 3 by antigen-antibody reaction, and the second antibody 12 on fine particles 13 bind to each other by antigen-antibody reaction. Thus, the first antibody 11 on the planar optical waveguide 3 and the second antibody 12 on fine particles 13 bind to each other via the antigen 15 by antigen-antibody reaction, leading to immobilization of the fine particles 13 on the surface of the planar optical waveguide 3.

If a red laser beam is irradiated from a red laser diode 21 through the incident-sided grating 2a onto the planar optical waveguide 3 and propagated through the planar optical waveguide 3 for generation of evanescent light in the region close to the surface (surface exposed in reaction hole 5) immediately after dropping of the analyte sample solution, the fine particles 13, which are immobilized on the planar optical waveguide 3, are present in the evanescent light region. Thus, the fine particles 13 are involved in absorption or scattering of the evanescent light, leading to decay in intensity of the evanescent light. As a result, the intensity of the red laser beam released the outgoing-sided grating 2b and received by the photodiode 22 declines gradually over time under the influence of the immobilized fine particles 13.

The deterioration rate in intensity of the laser beam received by the photodiode 22 is proportional to the amount of the fine particles 13 immobilized on the planar optical waveguide 3, i.e., the concentration of the antigen participating in the antigen-antibody reaction in the analyte sample solution 14. Therefore, a calibration curve showing the relationship between the antigen concentration and the deterioration rate in laser beam intensity is formed previously, by forming a curve showing deterioration in laser beam intensity over time by using an analyte sample solution having a known antigen concentration and determining the deterioration rate in laser beam intensity at a particular time on the curve. It is possible to determine the concentration of the antigen in the analyte sample solution by determining the deterioration rate in laser beam intensity at a particular time from the curve of deterioration in laser beam intensity over time as determined by the method and comparing the deterioration rate in laser beam intensity with the calibration curve.

Thus in the third embodiment, the present invention provides a method of measuring the analyte substance in the analyte sample, demanding a small amount of an analyte sample (e.g., 10 μL or less) and allowing quantitative determination of the concentration of the analyte substance in the analyte sample only by three operations of applying the analyte sample solution in the measurement region dropwise, washing, and applying fine particles dispersion dropwise into the measurement region.

In particular, the method in the third embodiment is useful when the concentration of the analyte substance in analyte sample solution (e.g., antigen) is high, because the washing is performed after dropwise addition of the analyte sample solution into the measurement region.

Fourth Embodiment

The method of measuring a substance according to the fourth embodiment will be described below.

First, an optical-waveguide sensor chip comprising an optical waveguide having a first substance immobilized on the surface thereof is prepared. The first substance is specifically reactive with an analyte substance. An analyte sample solution and fine particles having a second substance, which is specifically reactive with the analyte substance, immobilized on the surface thereof are previously mixed in a container such as a microtube to allow specific reaction between the second substance on the fine particles and the analyte substance in analyte sample solution. A liquid mixture obtained is then dropped on the surface of the optical waveguide of the sensor chip to allow specific reaction between the first substance on the optical waveguide and the analyte substance in analyte sample solution, which is bonded to the second substance on fine particles. The concentration of the analyte substance in the analyte sample solution is then determined by detecting the optical change caused by the fine particles immobilized on the surface of the optical waveguide via the first substance and the analyte substance, i.e., the fine particles immobilized on the surface of the optical waveguide.

For example, a planar optical waveguide can be used as the optical waveguide. As described in the first embodiment, the planar optical waveguide may be formed with a thermosetting resin or a nonalkali glass. A first substance reacting specifically with an analyte substance in the analyte sample is immobilized on the planar optical waveguide in a manner similar to the method described in the first embodiment. For example, if the analyte substance in the analyte sample is an antigen, the first substance for use may be an antibody.

As described in the first embodiment, fine particles may be used resin beads such as latex beads (the trade name) made of polystyrene, a metal colloid such as gold colloid, inorganic oxide particles such as titanium oxide particles, or the like. The fine particles may be also used, for example a protein such as an albumin, a polysaccharide such as an agarose, or a non-metal particle such as silica particle, a carbon particle. In particular, latex beads and noble metal colloids are preferable.

The fine particles preferably have a diameter of 50 nm to 10 μm.

A second substance is immobilized on the fine particles in a manner similar to that described in the first embodiment. For example, if the analyte substance in the analyte sample is an antigen, the second substance for use may be an antibody.

A dispersion of the fine particle may be prepared, for example, by dispersing the fin particles to buffer solutions containing phosphoric acid, trishydroxymethylaminomethane, boric acid, acetic acid, citric acid, carbonic acid or the like or a Good's buffer; those containing a stabilizer such as bovine serum albumin (BSA), casein, or polyethylene glycol and a nonionic surfactant such as Tween or Triton-X; phosphate-buffered physiological saline (PBS), and the like.

In mixing the analyte sample solution and fine particles having the second substance immobilized on the surface thereof, the fine particles may be presented in a state of dispersion, or in a state of solid (dry material, freeze material, or powder). Concretely, a dispersion of fine particles is previously prepared, and then an analyte sample solution and this dispersion may be mixed a container such as microtube. Further, in mixing an analyte sample solution and the dispersion of fine particles in a container such as microtube, a dispersion of fine particles contained a water-soluble substance may be poured in a container on a priority basis, drying (e.g., freeze drying) the dispersion therein to disperse the fin particles with water-soluble substance and then adding the analyte sample solution thereto for mixing. Examples of the water-soluble substance for use may include polyvinylalcohol, bovine serum albumin (BSA), polyethylene glycol, phospholipid polymers, gelatin, and sugars (e.g., sucrose, trehalose).

The measurement method according to the fourth embodiment will be described specifically with reference to the optical-waveguide sensor chip shown in FIG. 5 and also to FIGS. 7A and 7B.

Figure 7A:
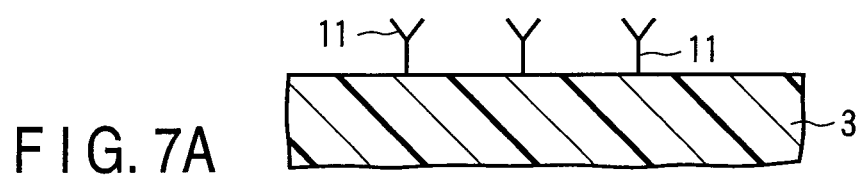
FIG. 7A and FIG. 7B are schematic views illustrating the step of measuring a substance in a fourth embodiment.
Figure 7B:
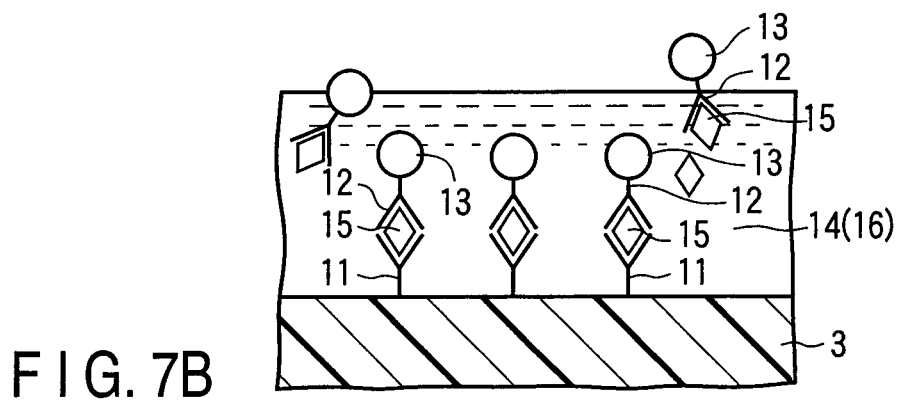

First as shown in FIGS. 5 and 7A, an optical-waveguide sensor is prepared. The sensor chip comprises a structure similar to that shown in the first embodiment, except that there is no dispersion layer of the fine particles shown in FIG. 1. Thus, it has a substrate 1 having gratings 2a and 2b. The planar optical waveguide 3 is formed on the major face of the substrate 1 containing gratings 2a and 2b. A low-refractive index resin film 4 is coated on the planar optical waveguide 3 and, for example, a rectangular reaction hole 5 is formed therein as an opening in such a way that part of the planar optical waveguide 3 located in the region between gratings 2a and 2b is exposed. A first substance (e.g., first antibody) 11 is immobilized on the surface of the planar optical waveguide 3 exposed in the reaction hole 5. The first antibody 11 is specifically reactive with the analyte substance in analyte sample (e.g., antigen). As shown in FIG. 5, a laser oscillator (e.g., red laser diode) 21 emitting light to the incident-sided grating 2a is installed for measurement of the change in evanescent light from the planar optical waveguide 3 in the region corresponding to the reaction hole 5, and a photoelectric conversion device (photodiode) 22 is installed for receiving the light from the outgoing-sided grating 2b. In addition, a dispersion of fine particles having a second substance (second antibody)

immobilized on the surface thereof is prepared. The second antibody is specifically reactive with the antigen.

An analyte sample solution and the dispersion of fine particles are previously mixed, for example, in a microtube to allow antigen-antibody reaction between the antigen in analyte sample solution and the second antibody on fine particles, thereby to obtain a liquid mixture. The liquid mixture is then dropped on the planar optical waveguide 3 in the reaction hole 5. Then as shown in FIG. 7B, the antigen 15 in the analyte sample solution that is bound to the second antibody previously in antigen-antibody reaction in the liquid mixture binds to the first antibody 11 on the surface of the planar optical waveguide 3 by antigen-antibody reaction. Thus, the antigen 15 bound to the second antibody 12 on fine particles 13 binds to the first antibody 11 on the surface of the planar optical waveguide 3 by antigen-antibody reaction, and consequently, the fine particles 13 are immobilized on the surface of the planar optical waveguide 3.

If a red laser beam is irradiated from a red laser diode 21 through the incident-sided grating 2a onto the planar optical waveguide 3 and propagated through the planar optical waveguide 3 for generation of evanescent light in the region close to the surface (surface exposed in reaction hole 5) immediately after dropping of the analyte sample solution, the fine particles 13, which are immobilized on the planar optical waveguide 3, are present in the evanescent light region. Thus, the fine particles 13 are involved in absorption or scattering of the evanescent light, leading to decay in intensity of the evanescent light. As a result, the intensity of the red laser beam released the outgoing-sided grating 2b and received by the photodiode 22 declines gradually over time under the influence of the immobilized fine particles 13.

The deterioration rate in intensity of the laser beam received by the photodiode 22 is proportional to the amount of the fine particles 13 immobilized on the surface of the planar optical waveguide 3, i.e., the concentration of the antigen participating in the antigen-antibody reaction in the analyte sample solution 14. Therefore, a calibration curve showing the relationship between the antigen concentration and the deterioration rate in laser beam intensity is formed previously, by forming a curve showing deterioration in laser beam intensity over time by using an analyte sample solution having a known antigen concentration and determining the deterioration rate in laser beam intensity at a particular time on the curve. It is possible to determine the concentration of the antigen in the analyte sample solution by determining the deterioration rate in laser beam intensity at a particular time from the curve of deterioration in laser beam intensity over time as determined by the method and comparing the deterioration rate in laser beam intensity with the calibration curve.

As described in the fourth embodiment, the present invention provides a method of measuring the analyte substance in the analyte sample, demanding a small amount of an analyte sample (e.g., 10 μL or less) and allowing quantitative determination of the concentration of the analyte substance in the analyte sample only by a single operation of applying the analyte sample solution and the fine particle dispersion in the measurement region dropwise.

The analyte sample solution and the dispersion of fine particles may be applied dropwise simultaneously onto the surface of an optical waveguide, instead of the analyte sample solution and the dispersion of fine particles to be applied dropwise on the surface of the optical waveguide being mixed with each other previously as in the fourth embodiment described above.

The analyte sample solution and the dispersion of fine particles are applied dropwise on the surface of an optical waveguide after mixing in the fourth embodiment described above, but the dispersion of fine particles may be applied after dropwise addition of the analyte sample solution, or alternatively, the analyte sample solution may be applied after dropwise addition of the dispersion of fine particles. It is possible to determine the concentration of the analyte substance in analyte sample even with a small amount (e.g., 10 μL or less) of analyte sample, independently of the order of addition, similarly to the fourth embodiment.

Fifth Embodiment

A substance-measuring kit according to the fifth embodiment will be described below.

The substance-measuring kit is a combination of:

(a) an optical-waveguide sensor chip comprising an optical waveguide having a first substance immobilized on the surface thereof, the first substance being specifically reactive with an analyte substance, and a cap formed on the optical waveguide and having a dent for forming a measurement region with the optical waveguide and having inlet and outlet holes for communication with the measurement region, and (b) a package accommodated a dispersion of fine particles having a second substance immobilized on the surface thereof, the second substance being specifically reactive with the analyte substance.

The first substance is immobilized on the planar optical waveguide in a manner similar to the method described in the first embodiment. For example if the analyte substance in the analyte sample is an antigen, the first substance for use may be an antibody.

As described in the first embodiment, the fine particles contained in the dispersion may be used resin beads such as latex beads (the trade name) made of polystyrene, a metal colloid such as gold colloid, inorganic oxide particles such as titanium oxide particles, or the like. The fine particles may be also used, for example a protein such as an albumin, a polysaccharide such as an agarose, or a non-metal particle such as silica particle, a carbon particle. In particular, latex beads and noble metal colloids are preferable. The fine particles preferably have a diameter of 50 nm to 10 μm.

The second substance is immobilized on the fine particles in a manner similar to that described in the first embodiment. For example, if the analyte substance in the analyte sample is an antigen, the second substance for use may be an antibody.

The dispersion of the fine particle include, for example, buffer solutions containing phosphoric acid, trishydroxymethylaminomethane, boric acid, acetic acid, citric acid, carbonic acid or the like, or a Good's buffer; those containing a stabilizer such as bovine serum albumin (BSA), casein, or polyethylene glycol and a nonionic surfactant such as Tween or Triton-X; or phosphate-buffered physiological saline (PBS), and the like.

The package is formed of, for example, a polyethylene film or a laminate film of polyethylene and polyethylene terephthalate. In addition, the package may be used a microtube, a plastic bottle or a glass bottle.

The substance-measuring kit according to the fifth embodiment will be described specifically with reference to FIGS. 8A and 8B. FIG. 8A is a top view illustrating the optical-waveguide sensor chip, and FIG. 8B is a cross-sectional view of the sensor chip shown in FIG. 8A.

The glass substrate 31 has an incident-sided grating 32a and an outgoing-sided grating 32b such as of titanium oxide formed on both terminals of the major face. A planar optical waveguide 33 such as of a thermosetting resin is formed on the major face of the substrate 31 having the gratings 32a and 32b. A cap 34 of a resin such as acrylic resin is formed, as it covers the major face and the side face of the planar optical waveguide 33. The cap 34 may be formed with another resin having a particular low-refractive index. The cap 34 has a rectangular dent 36 for forming, for example, a rectangular measurement region 35 on the surface of the planar optical waveguide 33. In addition, the cap 34 has an inlet hole 37 and an outlet hole 38 extending from the surface to the measurement region 35 formed therein. A first substance 11 is immobilized on the surface of the planar optical waveguide 33 exposed in the measurement region 35 by hydrophobilization treatment for example by using a silane-coupling agent. The first substance 11 is specifically reactive with an analyte substance in the analyte sample. Thus, a planar optical waveguide 33, a cap 34 and the like configure the optical-waveguide sensor chip.

The dispersion of fine particles having a second substance 12 immobilized on the surface thereof is placed for example in a polyethylene package (not shown in the figure), configures the measurement kit in combination with an optical-waveguide sensor chip described above. The second substance is specifically reactive with the analyte substance.

Hereinafter, the method of measuring a substance by using the kit described above will be described with reference to FIGS. 9A to 9C. For measurement of the change in evanescent light from the planar optical waveguide exposed in the measurement region, a laser oscillator (e.g., red laser diode) 21 emitting light to the incident-sided grating 32a is installed and also, a photoelectric conversion device (photodiode) 22 receiving the light from the outgoing-sided grating 32b is installed.

Figure 9A:
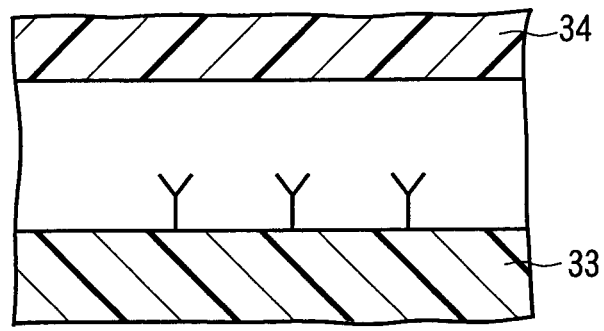
FIG. 9A, FIG. 9B and FIG. 9C are schematic views illustrating the step of measuring a substance in the fifth embodiment.

As shown in FIGS. 8 and 9A, an optical-waveguide sensor chip comprising a planar optical waveguide 33 having a first substance (e.g., first antibody) 11 immobilized on the surface of the planar optical waveguide 33 exposed in the measurement region 35 is prepared. The first antibody 11 is specifically reactive with an analyte substance (e.g., antigen) in analyte sample.

Figure 9B:
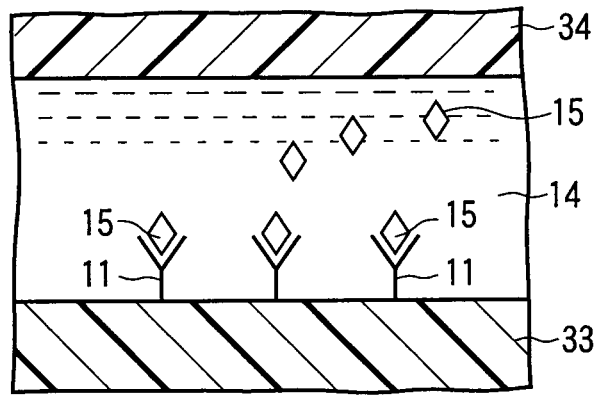

An analyte sample solution is then dropped through the inlet hole 37 into the measurement region 35. At this time as shown in FIG. 9B, the antigen 15 in the analyte sample solution 14 binds to the first antibody 11 on the surface of the planar optical waveguide 33 by antigen-antibody reaction.

Figure 9C:
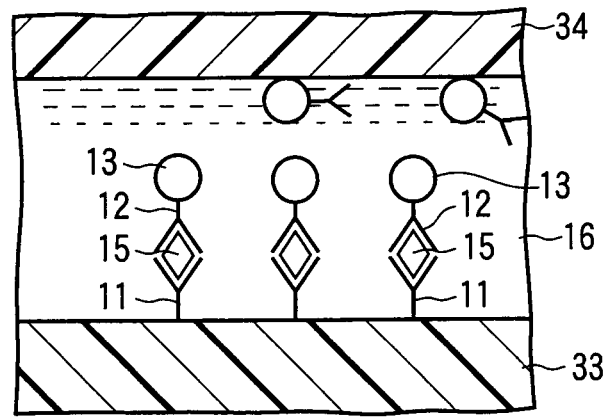

The dispersion 16 of fine particles in the package is introduced on the surface of the planar optical waveguide 33 in the measurement region 35 through the inlet hole 37 of cap 34, and the dispersion is discharged outward through the outlet hole 38. While the dispersion is discharged outward, the unreacted antigen remaining in the analyte sample solution is washed together with the dispersion. Simultaneously as shown in FIG. 9C, the second antibody 12 immobilized on the fine particles 13 in the dispersion 16 binds to the antigen, which is bound to the first antibody 11 on the surface of the planar optical waveguide 33, by antigen-antibody reaction. Thus, the fine particles 13 are immobilized on the surface of the planar optical waveguide 33, by binding between the first antibody 11 on the surface of the planar optical waveguide 33 and the second antibody 12 on fine particles 13 via antigen 15 by antigen-antibody reaction.

If a red laser beam is irradiated from a red laser diode 21 through the incident-sided grating 32a onto the planar optical waveguide 33 immediately after application of the dispersion of fine particles and propagated through the planar optical waveguide 33, generating evanescent light in the region close to the surface (surface exposed in measurement region 35).

The fine particles 13 in the dispersion 16 are immobilized on the surface of the planar optical waveguide 33, and thus, the fine particles 13 are present in the evanescent light region. Therefore, the fine particles 13 are involved in absorption or scattering of the evanescent light, leading to decay in intensity of the evanescent light. As a result, the intensity of the red laser beam released the outgoing-sided grating 32b and received by the photodiode 22 declines gradually over time under the influence of the immobilized fine particles 13.

The deterioration rate in intensity of the laser beam received by the photodiode 22 is proportional to the amount of the fine particles 13 immobilized on the surface of the planar optical waveguide 33, i.e., the concentration of the antigen participating in the antigen-antibody reaction in the analyte sample solution 14. Therefore, a calibration curve showing the relationship between the antigen concentration and the deterioration rate in laser beam intensity is formed previously, by forming a curve showing deterioration in laser beam intensity over time by using an analyte sample solution having a known antigen concentration and determining the deterioration rate in laser beam intensity at a particular time on the curve. It is possible to determine the concentration of the antigen in the analyte sample solution by determining the deterioration rate in laser beam intensity at a particular time from the curve of deterioration in laser beam intensity over time as determined by the method and comparing the deterioration rate in laser beam intensity with the calibration curve.

Accordingly, the substance-measuring kit in the fifth embodiment, which is combination of an optical-waveguide sensor chip in the structure permitting dropwise application of the analyte sample solution into the optical waveguide and the measurement region and the introduction and discharge of the dispersion of fine particles and a package containing the dispersion of fine particles, allows quantitative determination of the concentration of an analyte substance in a small amount (e.g., 10 μL or less) of analyte sample only with two operations of dropwise application of the analyte sample solution into the measurement region and introduction and discharge of the dispersion of fine particles into and from the measurement region.

Because the dispersion of fine particles is introduced and discharged into and from the measurement region after dropwise application of the analyte sample solution into the measurement region in the method of measuring the analyte substance in analyte sample by using the substance-measuring kit, the method is particularly effective when the concentration of the analyte substance in analyte sample solution (e.g., antigen) is high.

Hereinafter, Examples of the present invention will be described in detail with reference to the drawings above.

EXAMPLE 1

A titanium oxide film having a thickness of 50 nm was formed on a nonalkali glass substrate 1 having a refractive index of 1.52 by sputtering titanium oxide having a refractive index of 2.2 to 2.4, and gratings 2a and 2b were formed on the glass substrate 1 by lithography and dry etching. An epoxy resin solution was then spin-coated on the glass substrate 1 carrying the gratings 2a and 2b, to form a planar optical waveguide 3 having a thickness of approximately 30 μm by baking. The refractive index of the planar optical waveguide 3 after baking was 1.56. Subsequently, a commercially available low-refractive index resin, Cytop (registered trade name) poly(perfluorobutenylvinylether) manufactured by Asahi Glass Co., Ltd., was applied on the planar optical waveguide 3 by screen printing, to give a low-refractive index resin 4 having an rectangular reaction hole (measurement region) 5.

The surface of the planar optical waveguide 3 exposed in the reaction hole 5 was then hydrophobilized with a silane-coupling agent and an anti-insulin antibody 11 was immobilized thereon by hydrophobic interaction. A frame-shaped cell wall 6 was then formed on the low-refractive index resin 4, as it surrounds the reaction hole 5.

Blocking One (manufactured by Nacalai Tesque Inc.) was added to and diluted 2.5 times in phosphate buffered physiological saline (PBS), to give a solution. Anti-insulin antibody-immobilized blue latex beads having an average particle diameter of 760 nm were then dispersed in the solution, to give a bead dispersion having a bead dispersion concentration of 4 wt %. The Blocking One, which is a blocking agent for prevention of nonspecific adsorption, is an aqueous solution containing 4 to 8 wt % of tris(hydroxymethyl)aminomethane, 1 to 2 wt % of albumin, 2 to 6 wt % of casein, 10 wt % or less of a polymer compound, 1 wt % or less of an antiseptic substance and about 3 wt % of 4 M sodium hydroxide solution.

Then, 10 µL of the dispersion of the anti-insulin antibody-immobilized beads was added dropwise into the reaction hole 5, and the mixture was frozen preliminarily at −80° C. and freeze-dried for approximately 1 day, to give an optical-waveguide sensor chip carrying beads previously placed, as shown in FIG. 1. During the freeze drying, a disaccharide trehalose in an amount of 3 wt % and a surfactant Tween in an amount of 0.1 wt % were added to the bead dispersion in the composition above. These components were added for improvement in redispersibility of the bead dispersion.

Analyte sample solutions, i.e., insulin solutions at concentrations of 1.6 ng/mL and 6.4 ng/mL, were added dropwise respectively to the reaction hole on the obtained sensor chip in an amount of 10 µL, causing antigen-antibody reaction. The red light at a wavelength of 655 nm was irradiated from a red LED 21 through an incident-sided grating 2a into a planar optical waveguide 3 immediately after dropwise addition of the analyte sample solution; the light was propagated through the planar optical waveguide 3, generating evanescent light in the region close to the surface (surface exposed in reaction hole 5); and the red light from the outgoing-sided grating 2b was received by the photodiode 22 and the light intensity thereof was determined. Specifically, the change in light intensity over time was monitored.

The change in light intensity of an insulin solution at 6.4 ng/mL over time was monitored additionally thrice (total of four times). The results are summarized in FIG. 10.

Figure 10:
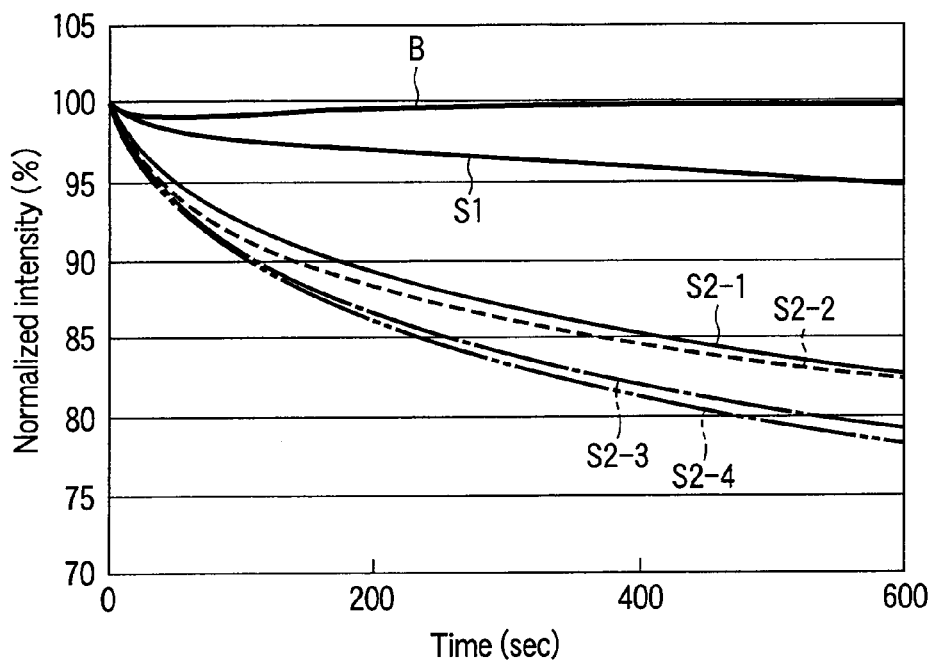
FIG. 10 is a graph showing a change in laser beam intensity over time in an insulin concentration measurement of Example 1.

In FIG. 10, the change in light intensity over time is shown, with respect to 100% of the light intensity immediately after dropwise addition of the analyte sample solution. In FIG. 10, the results obtained with an insulin solution at a concentration of 1.6 ng/mL are shown by S1, and the results of the four insulin solutions at a concentration of 6.4 ng/mL are shown respectively by S2-1, S2-2, S2-3 and S2-4. Additionally, a diluted insulin solvent (blank) was processed similarly as it was used as the analyte sample solution, and the change in laser beam intensity over time was determined, and the results are shown in FIG. 10 as indicated by B.

As obvious from FIG. 10, the rate of deterioration in laser beam intensity for a particular time has correlation with the insulin concentration in the analyte sample solution. The results obtained with the four analyte sample solutions at the same insulin concentration (6.4 ng/mL) also show that the rates of deterioration in laser beam intensity for a particular time are similar to each other, allowing concentration measurement at higher reproducibility.

EXAMPLE 2

A titanium oxide film having a thickness of 50 nm was formed on a nonalkali glass substrate 1 having a refractive index of 1.52 by sputtering titanium oxide having a refractive index of 2.2 to 2.4, and gratings 2a and 2b were formed on the glass substrate 1 by lithography and dry etching. An epoxy resin solution was then spin-coated on the glass substrate 1 carrying the gratings 2a and 2b, to form a planar optical waveguide 3 having a thickness of approximately 30 µm by baking. The refractive index of the planar optical waveguide 3 after baking was 1.56. Subsequently, a low-refractive index resin 4 having a rectangular reaction hole (measurement region) 5 was formed by applying a commercially available low-refractive index resin, Cytop (registered trade name) poly(perfluorobutenylvinylether) manufactured by Asahi Glass Co., Ltd., on the planar optical waveguide 3 by screen printing, to give an optical-waveguide sensor chip shown in FIG. 5.

Analyte sample solutions, i.e., insulin solutions at concentrations of 1.6 and 6.4 ng/mL, were added dropwise to the reaction hole of the obtained optical-waveguide sensor chip respectively in an amount of 10 µL and the mixtures were allowed to react at 37° C. for 10 minutes in antigen-antibody reaction. The excess insulin remaining in the reaction hole was washed with a washing buffer solution of tris-buffered physiological saline (TBS), and a bead dispersion similar to that in Example 1 was added dropwise to the reaction hole after washing in an amount of 20 µL. The change in light intensity from immediately after dropwise addition of the bead dispersion was monitored, similarly to Example 1 by using red LED 21 and photodiode 22.

Figure 11:
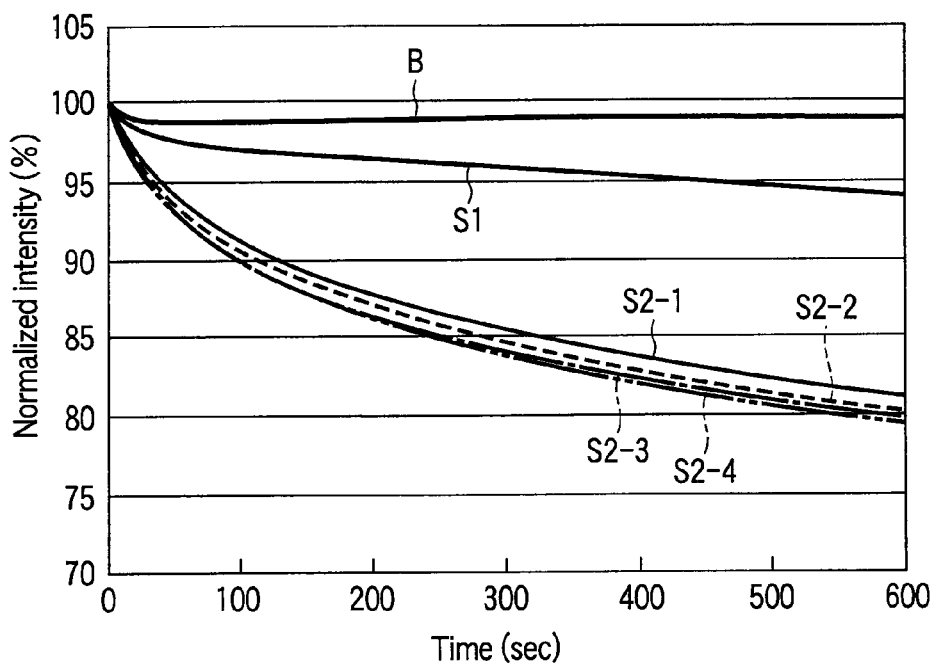
FIG. 11 is a graph showing a change in laser beam intensity over time in an insulin concentration measurement of Example 2.

The change in light intensity of an insulin solution at 6.4 ng/mL over time was monitored additionally thrice (total of four times), for measurement of the change in light intensity over time. In FIG. 11, the change in light intensity over time is shown, with respect to 100% of the light intensity immediately after dropwise addition of the analyte sample solution. In FIG. 11, the results of the insulin solution at a concentration of 1.6 ng/mL are shown by S1, and the results of the four insulin solutions at a concentration of 6.4 ng/mL are shown by S2-1, S2-2, S2-3 and S2-4. A diluted insulin solvent (blank) was processed similarly as it was used as the analyte sample solution; the change in laser beam intensity over time was determined; and the results are shown in FIG. 11 as indicated by B.

As obvious from FIG. 11, the rate of deterioration in laser beam intensity for a particular time has correlation with the insulin concentration in the analyte sample solution. The results obtained with the four analyte sample solutions at the same insulin concentration (6.4 ng/mL) show that the rates of deterioration in laser beam intensity for a particular time are similar to each other, allowing concentration measurement at higher reproducibility.

EXAMPLE 3

10 µL of a bead dispersion similar to that in Example 1 was added dropwise to the reaction hole of an optical-waveguide sensor chip similar to that in Example 2, and, immediately after that, analyte sample solutions, i.e., insulin solutions at concentrations of 1.6 ng/mL and 6.4 ng/mL, were added dropwise respectively in an amount of 10 µL and agitated by pipetting. Immediately after agitation, the change in light intensity was monitored similarly to Example 1 by using red LED 21 and photodiode 22.

The change in light intensity of an insulin solution at 6.4 ng/mL over time was monitored additionally thrice (total of four times), for measurement of the change in light intensity over time. In FIG. 12, the change in light intensity over time is shown, with respect to 100% of the light intensity immediately after dropwise addition of the analyte sample solution. In FIG. 12, the result of the insulin solution at a concentration of 1.6 ng/mL are shown by S1, and the results of the four insulin solutions at a concentration of 6.4 ng/mL are shown by S2-1, S2-2, S2-3 and S2-4. A diluted insulin solvent (blank) was also processed similarly as it was used as the analyte sample solution, and the change in laser beam intensity over time was determined, and the results are shown in FIG. 12 as indicated by B.

As obvious from FIG. 12, the rate of deterioration in laser beam intensity for a particular time has correlation with the insulin concentration in the analyte sample solution. The results obtained with the four analyte sample solutions at the same insulin concentration (6.4 ng/mL) show that the rates of deterioration in laser beam intensity for a particular time are similar to each other, allowing concentration measurement at higher reproducibility.

The results in Example 3 show that the deterioration rate in laser beam intensity is correlated with the insulin concentration in the analyte sample solution, similarly to Example 3, even when the order of adding the bead dispersion and the insulin solution dropwise was reversed or when the liquids were added dropwise simultaneously.

EXAMPLE 4

Previously, a bead dispersion similar to that in Example 1 was placed in a microtube in an amount of 50 μL and freeze-dried. During the freeze drying, a disaccharide trehalose in an amount of 3 wt % and a surfactant Tween in an amount of 0.1 wt % were added to the bead dispersion, similarly to Example 1. Analyte sample solutions, i.e., insulin solutions at concentrations of 1.6 ng/mL and 6.4 ng/mL were then added dropwise into the microtube respectively in an amount of 50 μL, and the mixture were agitated, allowing antigen-antibody reaction. Then, 20 μL of each liquid mixture in the microtube was added dropwise into a reaction hole of an optical-waveguide sensor chip similar to Example 2, which is shown in FIG. 5, the change in light intensity from immediately after dropwise addition was monitored similarly to Example 1 by using red LED 21 and photodiode 22.

A similar operation was repeated thrice (total of four times) with the 6.4 ng/mL insulin solution, for determination of the change in light intensity over time. In FIG. 13, the change in light intensity over time is shown, with respect to 100% of the light intensity immediately after dropwise addition of the analyte sample solution. In FIG. 13, the results of the insulin solution at a concentration of 1.6 ng/mL are shown by S1, and the results of the four insulin solutions at a concentration of 6.4 ng/mL are shown by S2-1, S2-2, S2-3 and S2-4. A diluted insulin solvent (blank) was processed similarly as it was used as the analyte sample solution; and the change in laser beam intensity over time was determined; and the results are shown in FIG. 13 as B.

As obvious from FIG. 13, the rate of deterioration in laser beam intensity for a particular time has correlation with the insulin concentration in the analyte sample solution. The results obtained with the four analyte sample solutions at the same insulin concentration (6.4 ng/mL) show that the rates of deterioration in laser beam intensity for a particular time are similar to each other, allowing concentration measurement at higher reproducibility.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical-waveguide sensor chip, comprising:
   a planar optical waveguide configured to generate evanescent light by propagating incident light therein;
   a first substance immobilized on the surface of the optical waveguide, and which is specifically reacted with an analyte substance in an analyte sample; and
   fine particles dispersed on the optical waveguide and having a second substance immobilized on the surface thereof, the second substance being specifically reacted with the analyte substance in the analyte sample,
   wherein the fine particles have a diameter of 760 nm to 10 μm.

2. The optical-waveguide sensor chip according to claim 1, wherein the optical waveguide is made of glass.

3. The optical-waveguide sensor chip according to claim 1, wherein the optical waveguide is an organic resin film having a thickness of 3 to 300 μm.

4. The optical-waveguide sensor chip according to claim 1, wherein the fine particles are resin beads.

5. The optical-waveguide sensor chip according to claim 1, wherein the fine particles are metal colloids.

6. The optical-waveguide sensor chip according to claim 1, wherein the analyte substance in the analyte sample is an antigen and each of the first and second substances, which is specifically reactive with the analyte substance, is antibodies.

7. The optical-waveguide sensor chip according to claim 1, further comprising a blocking layer formed on the optical waveguide, the fine particles being dispersed on the surface of the blocking layer.

8. The optical-waveguide sensor chip according to claim 7, wherein the blocking layer comprises a water-soluble substance.

9. The optical-waveguide sensor chip according to claim 1, wherein the fine particles are at least partly dispersed on an area in which the evanescent light is emitted from the optical waveguide.

\* \* \* \* \*